United States Patent [19]

Haugwitz et al.

[11] 4,328,241
[45] May 4, 1982

[54] SUBSTITUTED PHENYLGUANIDINES AND METHOD

[75] Inventors: Rudiger D. Haugwitz; Barbara V. Maurer, both of Titusville, N.J.

[73] Assignee: E. R. Squibb & Sons, Inc., Princeton, N.J.

[21] Appl. No.: 284,741

[22] Filed: Jul. 20, 1981

[51] Int. Cl.$^3$ .................. C07C 147/14; A61K 31/325
[52] U.S. Cl. ................................ 424/300; 260/397.6; 560/13
[58] Field of Search ....................... 560/13; 424/300; 260/397.6

[56] References Cited

U.S. PATENT DOCUMENTS 3,828,094  8/1974  Widdig et al.
3,993,682  11/1976  Kolling et al.
4,024,176  5/1977  Kolling et al.
4,246,260  1/1981  Kolling et al.

Primary Examiner—Michael Shippen

Attorney, Agent, or Firm—Lawrence S. Levinson; Burton Rodney

[57] ABSTRACT

Phenylguanidine derivatives are provided having the structure

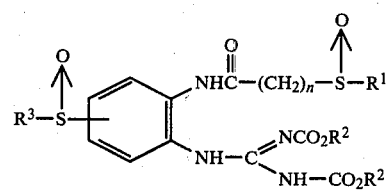

wherein $R^1$ is lower alkyl, cycloalkylalkyl, or phenylalkyl; $R^2$ is lower alkyl, phenyl or benzyl; and $R^3$ is lower alkyl, cycloalkylalkyl, lower alkenylalkyl, dihalovinylalkyl, dihalobutadienyl or phenylalkyl; and n is 1 to 5. These compounds are useful as anthelmintic agents.

9 Claims, No Drawings

SUBSTITUTED PHENYLGUANIDINES AND METHOD

DESCRIPTION OF THE INVENTION

The present invention relates to phenylguanidine derivatives which are useful as anthelmintic agents and have the structure

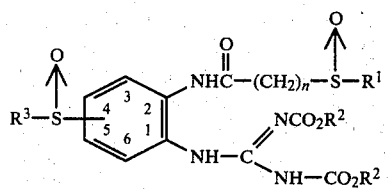

wherein $R^1$ is lower alkyl, cycloalkylalkyl, or phenylalkyl; $R^2$ is lower alkyl, phenyl or benzyl; $R^3$ is lower alkyl, cycloalkylalkyl, lower alkenylalkyl, dihalovinylalkyl, dihalobutadienyl or phenylalkyl; and n is 1 to 5.

The term "lower alkyl" or "alkyl" as used herein whether employed as an independent substituent or as a part of another substituent includes straight or branched chain aliphatic hydrocarbon radicals having up to and including 7 carbon atoms, preferably 1 to 3 carbons, such as methyl, ethyl, propyl, isopropyl, butyl, isobutyl, t-butyl, amyl, hexyl, heptyl and the like.

The term "phenylalkyl" as used herein refers to lower alkyl groups as discussed above having a phenyl substituent, such as benzyl.

The term "cycloalkylalkyl" refers to lower alkyl groups defined above having a cycloalkyl substituent which includes cyclic hydrocarbon groups containing 3 to 12 carbons, which include cyclopropyl, cyclobutyl, cyclopentyl, cyclohexyl, cycloheptyl, cyclooctyl, cyclodecyl and cyclododecyl, any of which groups may be substituted with 1, 2, 3 or 4 halogen and/or 1, 2, 3 or 4 lower alkyl groups.

The term "lower alkenylalkyl" refers to lower alkyl groups as defined above having a lower alkenyl substituent which is an unsaturated hydrocarbon group having from 3 to 6 carbon atoms and a single carbon-carbon double bond. Typical alkenyl substituents include, for example, 2-propenyl, 1-propenyl, 1-butenyl, 2-butenyl, 3-butenyl, and the like.

The term "dihalovinylalkyl" refers to groups of the structure $X_2C=CH\text{-alkyl-}$ wherein X represents Cl, Br or F and alkyl is as defined above. Typical dihalovinylalkyl groups include, for example, dichlorovinylpropyl, dibromovinylpropyl, dichlorovinylbutyl and dibromovinylbutyl.

The term "dihalobutadienyl" refers to groups of the structure

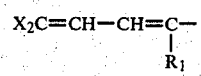

wherein X is as defined above and $R_1$ is H or alkyl. Typical dihalobutadienyl groups include, for example, dichlorobutadienyl and dibromobutadienyl and 1,1-dichloro-4-methylbutadienyl.

Preferred are those compounds wherein $R^1$ is lower alkyl such as methyl or ethyl, benzyl or cyclopropylmethyl, $R^2$ is lower alkyl such as methyl or ethyl, or benzyl, $R^3$ is cycloalkylalkyl such as cyclopropylmethyl, cyclobutylmethyl, 2,2-dichloro-1-methylcyclopropylmethyl, or lower alkyl, such as 2-methylpropyl or isopropyl, and n is 1 or 2.

The compounds of structure I may be conveniently prepared from phenylguanidines II which upon oxidation with m-chloroperbenzoic acid or oxidizing agents such as $NaIO_4$ yield I.

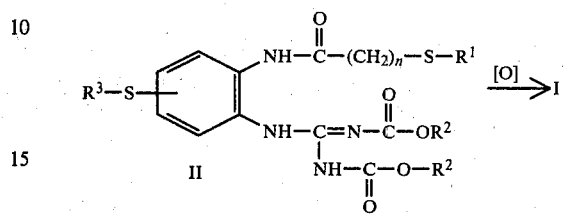

Phenylguanidines II may be prepared in a two-step reaction sequence from nitrosulfides V. The first step involves the catalytic reduction of the nitro group with hydrogen and platinum or chemical reduction with dithionite or zinc and acetic acid to yield the aniline derivative III which in turn is reacted with the S-methyl isothiourea IV to furnish II.

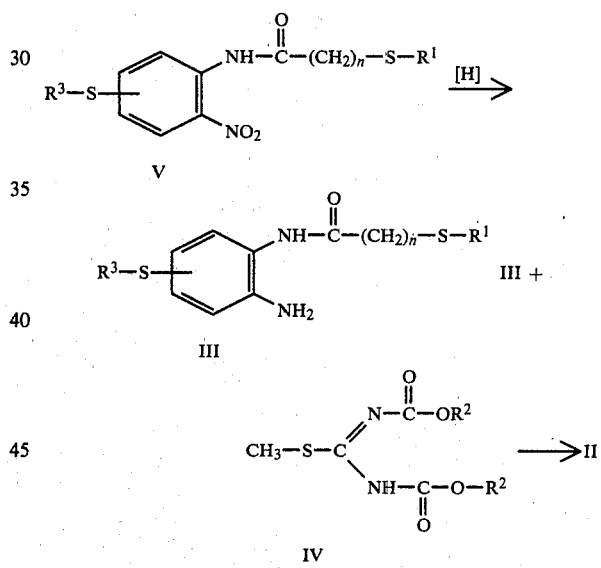

The above reaction of III and IV is carried out, optionally, in the presence of an acid such as p-toluenesulfonic acid or acetic acid, and preferably at temperatures ranging from about 50° to about 100° C. for periods ranging from about 1 to about 5 hours.

The formula V nitro derivatives are synthesized by acylating the nitroaniline compound of the structure VI

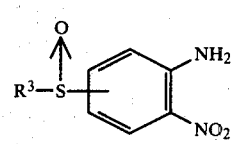

with an acid derivative VII

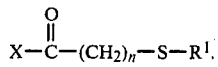

$$X-\overset{\overset{O}{\|}}{C}-(CH_2)_n-S-R^1. \quad \text{VII}$$

Whereas the 5-substituted nitroanilines VI may be prepared by reacting 5-halo-2-nitroaniline VIII and the appropriate thiol IX,

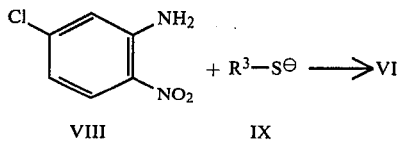

4-substituted nitroanilines VI may be synthesized from 4-mercapto-2-nitroaniline VIIIa and the requisite haloalkane derivatives

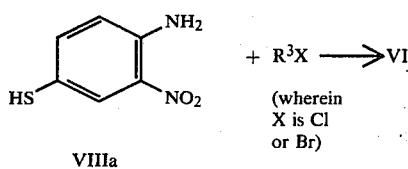

(wherein X is Cl or Br)

Other starting materials employed in the above reactions are either known in the art or easily prepared according to conventional techniques.

In certain instances, the compounds of formula I form physiologically acceptable acid-addition salts with inorganic and organic acids. These salts frequently provide useful means for isolating the products from reaction mixtures by forming the salt in a medium in which it is insoluble. The free base may then be obtained by neutralization. Then any other salt may again be formed from the free base and the appropriate inorganic acid. Illustrative are the hydrohalides, especially the hydrochloride and hydrobromide which are preferred, sulfate, nitrate, tartrate, methanesulfonate, benzenesulfonate, toluenesulfonate, and the like.

The compounds of formula I have anthelmintic activity and are useful in the treatment and/or prevention of helminthiasis, a parasitic disease which causes widespread and often serious infection in domesticated animals such as swine, horses, cattle, dogs, cats and sheep. The compounds are useful in treating infections caused by Haemonchus, Ostertagia, Trichostrongylus, Cooperia, Dictyocaulus, Nematodirus, Bunostomum, Strongyloides, Oesophagostomum, Trichuris, Moniezia, and liver flukes (for example in sheep). In treating domesticated animals, the compounds are given orally; however, other routes such as parenterally, for example, subcutaneously, intravenously, interperitoneally and intramuscularly may be employed.

Where the compounds are administered orally, they may be mixed with a nontoxic, edible carrier to form a feed supplement, or may be administered in unit dosage forms such as powders, capsule, tablet, boluses, drenches, etc.

Where the compounds are administered parenterally, they may be dispersed (for example, suspended) in nontoxic non-pyrogenic physiologically acceptable carriers such as water, benzyl benzoate, 1,3-butylene glycol, ethyl oleate, glyceryl triacetate, castor oil, sesame oil, and sesame oil: benzyl benzoate (1:1). The parenteral product will usually take the form of a suspension containing from about 1 to about 10% by weight of the compound of formula I in anyone or mixture of the above carriers.

In general, the compounds of formula I exhibit anthelmintic activity when administered to animals (parenterally or orally) in a single dose of about 1 to about 100 mg per kilogram of animal body weight. It is preferred to employ in the range of 2.5-25 mg per kilogram of body weight. The compounds may be divided into a plurality of smaller doses given parenterally or orally over one or more days.

When the compounds of formula I are to be administered in unit dosage form, capsules, boluses or drenches containing the desired amount of anthelmintic distributed in a pharmaceutically acceptable vehicle are usually employed. These are prepared by intimately and uniformly mixing the active ingredient with suitable finely divided diluents, suspending agents, fillers, disintegrating agents and/or binders such as starch, lactose, talc, magnesium stearate, vegetable gums and the like and are compounded by techniques generally known in the art.

The compounds of formula I may also be administered as a component of the feed of the animals or suspended in the drinking water. Thus, novel feed and feed supplement compositions may be prepared in which the compounds of this invention are present as an active anthelmintic ingredient. A typical feed supplement comprises the anthelmintic agent intimately dispersed in or admixed with an inert carrier or diluent, i.e., one that is nonreactive with respect to the anthelminitc agent and that may be administered with safety to the animals. The carrier or diluent is preferably one that is or may be an ingredient of an animal ration. This composition may be mixed with the feed to give any useful desired concentration, preferably about 0.1-2%. Lastly, feeds containing the active ingredient may be made directly by mixing said active ingredient in a feed which is inert to said anthelmintic compounds so as to give feeds having concentrations of anthelmintic agent of from 0.1-2%.

The following examples are provided for illustrative purposes and may include particular features of the invention, however, the examples should not be construed as limiting the invention, many variations of which are possible without departing from the spirit or scope thereof. All temperatures are in degrees centigrade.

EXAMPLE 1

[[[2-[[(Methylsulfinyl)acetyl]amino]-4-[(2-methylpropyl)sulfinyl]phenyl]amino][(methoxycarbonyl)amino]methylene]carbamic acid, methyl ester A. Methylmercaptoacetic acid A mixture of 27 g of mercaptoacetic acid, 46 g methyl iodide and 600 ml of 1 N NaOH is stirred for 48 hours at R.T. The mixture is extracted with ether to remove excess methyl iodide. The aqueous phase is then acidified and extracted with ether. The organic fractions are combined, dried, filtered and evaporated. The oily residue is distilled: $bp_{30}$ 130°–132° (Lit. $bp_{27}$ 131°–132°); yield 22 g.

B. Methylmercaptoacetyl chloride

A mixture of 20 g methylmercapto acetic acid and 20 ml of $SOCl_2$ is refluxed for 1 hour. Excess $SOCl_2$ is removed in vacuo. To the residue there is added benzene, which then is evaporated. This procedure is repeated. The resulting oil is distilled; bp$_{15}$ 48°-50° (Lit. bp$_{14}$ 49°-50°); yield: 8.3 g.

C.
2-(Methylmercaptoacetylamino)-4-[(2-methylpropyl)-thio]nitrobenzene

A mixture of 11.5 g 2-nitro-b 5-[(2-methylpropyl)-thio]aniline and 6.2 g of methylmercaptoacetyl chloride is heated gently on the steam bath for 0.5 hour. The slurry is dissolved in boiling ether, filtered and cooled to yield 12.8 g; m.p. 73°-74°.

D.
2-(Methylmercaptoacetylamino)-4-[(2-methylpropyl)-thio]aniline

A mixture of 12.4 g of 2-(methylmercaptoacetylamino)-4-[(2-methylpropyl)thio]nitrobenzene, 1.3 g PtO$_2$ and 200 ml of ethanol is reduced on the Parr hydrogenator at 50 psi until the required amount of H$_2$ is absorbed. The mixture is filtered, the solvent removed and the residue used immediately in the next reaction.

E.
[[[2-[[(Methylmercapto)acetyl]amino]-4-[(2-methylpropyl)thio]phenyl]amino][(methoxycarbonyl)amino]-methylene]carbamic acid, methyl ester To a solution of the above aniline in 100 ml of methanol there is added 8.0 g of N,N'-bis-methoxycarbonyl-S-methyl-isothiourea and 1 ml of acetic acid. This mixture is refluxed for 3 hours, filtered hot and the filtrate partly evaporated. The resulting solid is filtered off and washed with ether. Yield 6.4 g m.p. 138°-140°.

F.
[[[2-[[(Methylsulfinyl)acetyl]amino]-4-[(2-methylpropyl)sulfinyl]phenyl]amino]-[(methoxycarbonyl)amino]methylene]carbamic acid, methyl ester To a solution of 4.4 g of the above sulfide in 200 ml of CH$_2$Cl$_2$ there is added 4.0 g of m-chloroperbenzoic acid at 0°. The mixture is then stirred for three hours at R.T. The organic phase is washed with a 5% K$_2$CO$_3$ solution, then with water to pH 7. The organic phase is dried, filtered and evaporated. Trituration of the residue with ethanol yields the title compound in the form of a solid, m.p. 149°-150°; yield 75%.

EXAMPLES 2 TO 6

Following the procedure of Example 1 and substituting the methylthioacetyl chloride the acid halides in the first column of Table I set out below, the products depicted in the second column are obtained.

TABLE I

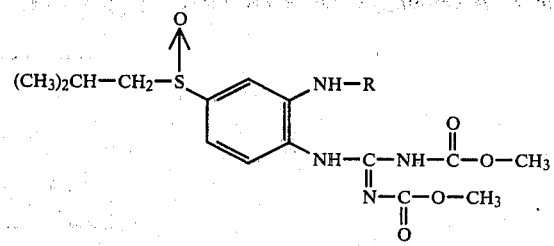

Column II

| Ex. No. | Column I Acid Halide | R |
|---|---|---|
| 2. | C$_2$H$_5$SCH$_2$COCl | C$_2$H$_2$SCH$_2$CO— |
| 3. | C$_6$H$_5$SCH$_2$COBr | C$_6$H$_5$SCH$_2$CO— |
| 4. | (CH$_3$)$_2$CHCH$_2$SCH$_2$COCl | (CH$_3$)$_2$CHCH$_2$SCH$_2$CO— |
| 5. | CH$_3$SCH$_2$CH$_2$COCl | CH$_3$SCH$_2$CH$_2$CO— |
| 6. | CH$_3$—S—CH$_2$COCl | CH$_3$SCH$_2$CO— |

(In Column II each R group is attached via a C=O with an O above as shown in the table.)

EXAMPLES 7 TO 9

Following the procedure of Example 1 and substituting for 5[(2-methylpropyl)thio]-2-nitroaniline, 4-[(cyclopropylmethyl)thio]-2-nitroaniline and for acetyl chloride the acid halides in the first column of Table II set out below, the products shown in the second column are obtained.

TABLE II

Column II

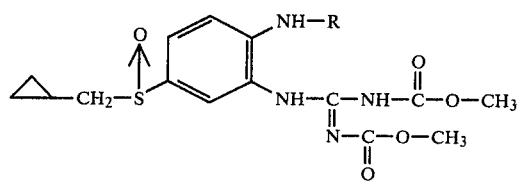

| Ex. No. | Column I Acid Halide | R |
|---|---|---|
| 7. | CH₃SCH₂COBr | CH₃SCH₂CO (with O↑) |
| 8. | C₆H₅CH₂SCH₂COCl | C₆H₅CH₂S—CH₂CO (with O↑) |
| 9. | CH₃SC₂H₄COCl | CH₃SC₂H₂CO (with O↑) |

EXAMPLES 10 TO 25

Following the procedure of Example 1 but substituting for 5-[(2-methylpropyl)thio]-2-nitroaniline, the aniline derivative shown in Column I of Table III set out below, substituting for methylmercapto acetyl chloride, the compound shown in Column II, and substituting for N,N'-bis-methoxycarbonyl-S-methyl-isothiourea, the compound shown in Column III, the product in accordance with the present invention shown in Column IV is obtained.

TABLE III

| Ex. No. | Column I: $R^3$ (position of $R^3$—S) | Column II: $R^1$ | n |
|---|---|---|---|
| 10. | Cl₂C=CH(CH₂)₃— (5) | C₂H₅ | 1 |
| 11. | ▷—CH₂ (5) | C₆H₅CH₂ | 1 |
| 12. | CH₂=CH—CH₂ (5) | C₆H₅(CH₂)₂ | 2 |
| 13. | (CH₃)₂CHCH₂ (5) | C₂H₅ | 2 |
| 14. | CH₃ (4) | ▢—CH₂— | 3 |
| 15. | Cl,Cl-cyclopropyl-CH₂— (5) | C₆H₅CH₂ | 3 |
| 16. | Cl₂C=CH—CH=C(CH₃)— | CH₃ | 4 |

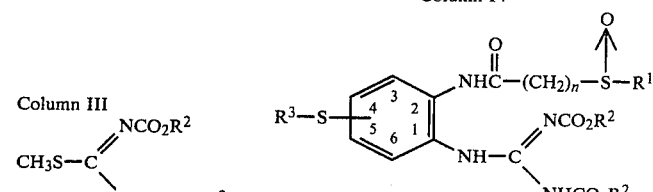

| Ex. No. | Column III: $R^2$ | $R^3$ | (position of $R^3$—S) | $R^1$ and n | $R^2$ |
|---|---|---|---|---|---|
| 10. | CH₃ | as in Column I | (4) | as in Column II | as in Column III |
| 11. | CH₃ | | (4) | | |
| 12. | CH₃ | | (4) | | |
| 13. | C₆H₅CH₂ | | (4) | | |
| 14. | CH₃ | | (5) | | |
| 15. | C₆H₅(CH₂)₂ | | (4) | | |

TABLE III-continued

| Ex. No. | | | |
|---|---|---|---|
| 16. | Cl₂C=CH—CH=C(CH₃)— | | (4) |

| Ex. No. | Column I R³ (position of R³—S) | Column II R¹ | n |
|---|---|---|---|
| 17. | C₆H₅CH₂ (4) | C₆H₅CH₂ | 4 |
| 18. | (Cl)(Cl)C₂—CH₂— (5) [dichlorocyclopropylmethyl] | C₂H₅ | 5 |
| 19. | (CH₃)₂CH— (5) | CH₃ | 5 |
| 20. | Cl₂C=CH—CH=CH— (5) | i-C₃H₇ | 1 |
| 21. | cyclopropyl-CH₂ (5) | C₆H₅CH₂— | 1 |
| 22. | CH₂=CHCH₂ (5) | C₆H₅CH₂— | 5 |
| 23. | cyclobutyl-CH₂ (5) | cyclopropyl-CH₂— | 2 |
| 24. | (Cl)(Cl)C₂—CH₂— (5) [dichlorocyclopropylmethyl] | C₆H₅CH₂ | 3 |
| 25. | CH₂=CH—CH₂ (5) | CH₃ | 4 |

| Ex. No. | Column III R² | Column IV | | | |
|---|---|---|---|---|---|
| | | R³ | (position of R³—S) | R¹ and n | R² |
| 17. | CH₃ | as in Column I | (5) | as in Column II | as in Column III |
| 18. | C₆H₅ | | (4) | | |
| 19. | C₂H₅ | | (4) | | |
| 20. | CH₃ | | (4) | | |
| 21. | C₂H₅ | | (4) | | |
| 22. | C₆H₅ | | (4) | | |
| 23. | CH₃ | | (4) | | |
| 24. | CH₃ | | (4) | | |
| 25. | CH₃ | | (4) | | |

What is claimed is:

1. A compound of the structure

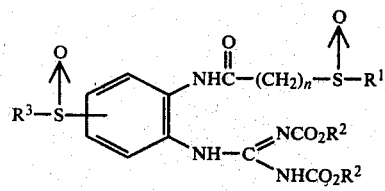

wherein $R^1$ is lower alkyl, cycloalkylalkyl, or phenylalkyl; $R^2$ is lower alkyl, phenyl or benzyl; and $R^3$ is lower alkyl, cycloalkylalkyl, lower alkenylalkyl, dihalovinylalkyl, dihalobutadienyl or phenylalkyl, and n is 1 to 5, and physiologically acceptable salts thereof.

2. The compound as defined in claim 1 wherein n is 1.

3. The compound as defined in claim 1 wherein n is 2.

4. The compound as defined in claim 1 wherein $R^1$ is lower alkyl, $R^2$ is lower alkyl, $R^3$ is lower alkyl and n is 1 or 2.

5. The compound as defined in claim 1 having the name [[[2-[[(methylsulfinyl)acetyl]amino]-4-[(2-methylpropyl)sulfinyl]phenyl]amino][(methoxy carbonyl)amino]methylene]carbamic acid, methyl ester.

6. An anthelmintic composition comprising a therapeutic amount of a compound as defined in claim 1 and a pharmaceutically acceptable carrier therefor.

7. A method for treating or preventing helminth infestation in mammalian hosts which comprises administering to a mammal a therapeutic amount of an anthelmintic composition as defined in claim 1.

8. The method as defined in claim 6 wherein said composition is administered orally or parenterally.

9. The method as defined in claim 8 wherein said composition is administered parenterally.

* * * * *